(12) United States Patent
Geiger et al.

(10) Patent No.: US 10,512,652 B2
(45) Date of Patent: Dec. 24, 2019

(54) USE OF CYMANQUINE COMPOUNDS AS ANTIMALARIAL AGENTS

(71) Applicants: University of Vermont and State Agricultural College, Burlington, VT (US); Drexel University, Philadelphia, PA (US)

(72) Inventors: William E. Geiger, Williston, VT (US); Kevin Lam, Genval (BE); Lawrence W. Bergman, Landsdale, PA (US)

(73) Assignees: University of Vermont and State Agricultural College, Burlington, VT (US); Drexel University, Philadelphia, PA (US)

( * ) Notice: Subject to any disclaimer, the term of this patent is extended or adjusted under 35 U.S.C. 154(b) by 0 days.

(21) Appl. No.: 15/745,938

(22) PCT Filed: Jul. 20, 2016

(86) PCT No.: PCT/US2016/043100
§ 371 (c)(1),
(2) Date: Jan. 18, 2018

(87) PCT Pub. No.: WO2017/015344
PCT Pub. Date: Jan. 26, 2017

(65) Prior Publication Data
US 2018/0214457 A1    Aug. 2, 2018

Related U.S. Application Data

(60) Provisional application No. 62/194,559, filed on Jul. 20, 2015.

(51) Int. Cl.
*A61K 31/555* (2006.01)
*A61P 33/06* (2006.01)

(52) U.S. Cl.
CPC ............ *A61K 31/555* (2013.01); *A61P 33/06* (2018.01); *Y02A 50/411* (2018.01)

(58) Field of Classification Search
CPC ...... A61K 31/555; A61P 33/06; Y02A 50/411
See application file for complete search history.

(56) References Cited

U.S. PATENT DOCUMENTS

| 2010/0216727 A1 | 8/2010 | Adam et al. |
| 2012/0258945 A1 | 10/2012 | Fraisse et al. |
| 2018/0022771 A1* | 1/2018 | Geiger .................. A61K 45/06 514/187 |

FOREIGN PATENT DOCUMENTS

| WO | 2008/130261 A1 | 10/2008 |
| WO | 2016/109849 A1 | 7/2016 |

OTHER PUBLICATIONS

Arancibia, R., et al., Synthesis and antimalarial activities of rhenium bioorganometallics based on the 4-aminoquinoline structure, Bioorganic & Medicinal Chemistry, Sep. 19, 2010, vol. 18, pp. 8085-8091. http://sciencedirect.com/science/article/pii/S0968089610008205.
Lam, K., et al., Synthesis and anodic electrochemistry of cymanquine and related complexes, Journal of Organometallic Chmistry, May 11, 2016, vol. 817, pp. 15-20. http://www.sciencedirect.com/science/article/pii/S0022328X16301954.

* cited by examiner

*Primary Examiner* — Umamaheswari Ramachandran
(74) *Attorney, Agent, or Firm* — Hodgson Russ LLP

(57) ABSTRACT

Organometallic compounds comprising a chloroquinoline moiety for use in the prophylaxis and treatment of malaria. The compounds can be manganese or rhenium complexes of a ligand comprising a chloroquinoline moiety.

13 Claims, 9 Drawing Sheets

USE OF CYMANQUINE COMPOUNDS AS ANTIMALARIAL AGENTS

CROSS-REFERENCE TO RELATED APPLICATIONS

This application claims priority to U.S. Provisional application No. 62/194,559, filed on Jul. 20, 2015, the disclosure of which is incorporated herein by reference.

BACKGROUND OF THE DISCLOSURE

Malaria is one of the leading causes of morbidity and mortality worldwide, affecting millions of people annually. A major problem in treating malaria arises from the fact that some blood parasites that cause the disease have become resistant to the commonly used antimalarial drugs. Therefore, there is a need for new chemical agents that are strongly active against the parasitic protozoans responsible for malaria infections, most notably *Plasmodium falciparum* (*P. falciparum*), the resistant parasite responsible for the greatest number of deaths from malaria.

Chloroquine (CQ, 1) and hydroxychloroquine (HCQ, 1a) are known for their antimalarial activities and as inhibitors of autophagy in mammalian cells. Ferroquine (FQ, 2), which reached phase IIb trials, and structurally-modified ferroquines have also been intensely studied as antimalarials. (parasitesandvectors.com/content/7/1/424).

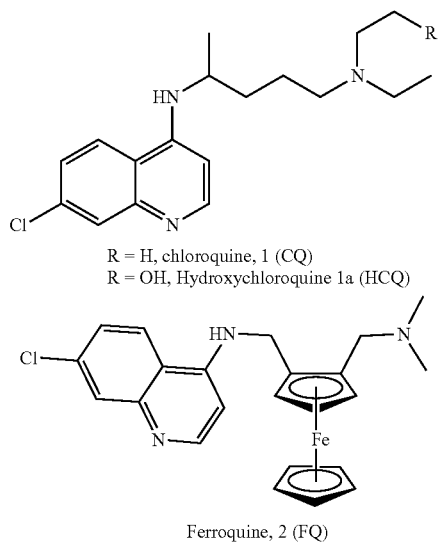

R = H, chloroquine, 1 (CQ)
R = OH, Hydroxychloroquine 1a (HCQ)

Ferroquine, 2 (FQ)

SUMMARY OF THE DISCLOSURE

The present disclosure provides a method of treating or reducing the risk of developing malaria. The method comprises administering to an individual in need thereof, a composition comprising compounds related to, but distinct from, CQ and FQ, containing a transition metal core. In one embodiment, the core metal is manganese (e.g., 3, 4, and 5). These manganese compounds are fundamentally different from existing technologies in terms of critical aspects of their chemical structures: (1) unlike all of the historically important, as well as the present state-of-the-art antimalarial drugs, they are not strictly organic compounds. They contain an organometallic moiety (or 'group') that is flexibly linked to an organic moiety. In the present context, we refer to this class of compounds as "mixed organic/organometallic" (MOOM) compounds. (2) Unlike FQ, the new compounds contain a manganese atom and two to three carbonyl ligands that are bonded to manganese. Or, they may contain a rhenium atom in place of the manganese atom. (3) Unlike other known manganese-containing MOOM compounds, the new compounds have an organic-to-organometallic linkage (—$CH_2NH$—) which is similar to that of ferroquine. Thus, the present compounds have a unique combination of organic group, organometallic group, and organic-to-organometallic linkage.

An advantage of the compounds of the present disclosure is that they have chemical, structural, and reactive properties that diverge from antimalarials of either the purely organic or ferroquine-MOOM type. The organometallic unit of cymanquine is highly lipophilic, which promotes its penetration of cellular membranes. Unlike ferroquine, it is not susceptible to Fenton-type chemical reactions, which often furnish toxic hydroxyl radicals that may give rise to unwanted side effects. The manganese center of cymanquine is not readily oxidized under biological conditions and is therefore less prone to give radical-based complications to the medical treatment. The fact that the manganese-tricarbonyl group of 3 has an inherently smaller structural "cone" than the iron-cyclopentadienyl group of 2 may minimize problems of steric bulk that could impede membrane crossing. Thus, the cymanquine family offers (i) a new group of drug candidates having chemical and physical properties that differ sufficiently from those of existing antimalarials to be effective against resistant blood parasites (ii) an excellent ability to cross cell membranes, a key factor in providing rapid and effective chemical effects and (iii) a low tendency to undergo in-vivo oxidation-based radical reactions, thereby minimizing or eliminating some unwanted side effects.

BRIEF DESCRIPTION OF THE DRAWINGS

FIG. 1 is the $^1H$ spectrum, and FIG. 2 is the $^{13}C$ spectrum.

FIG. 3 is the $^1H$ spectrum, and FIG. 4 is the $^{13}C$ spectrum.

DESCRIPTION OF THE DISCLOSURE

Figure 1:
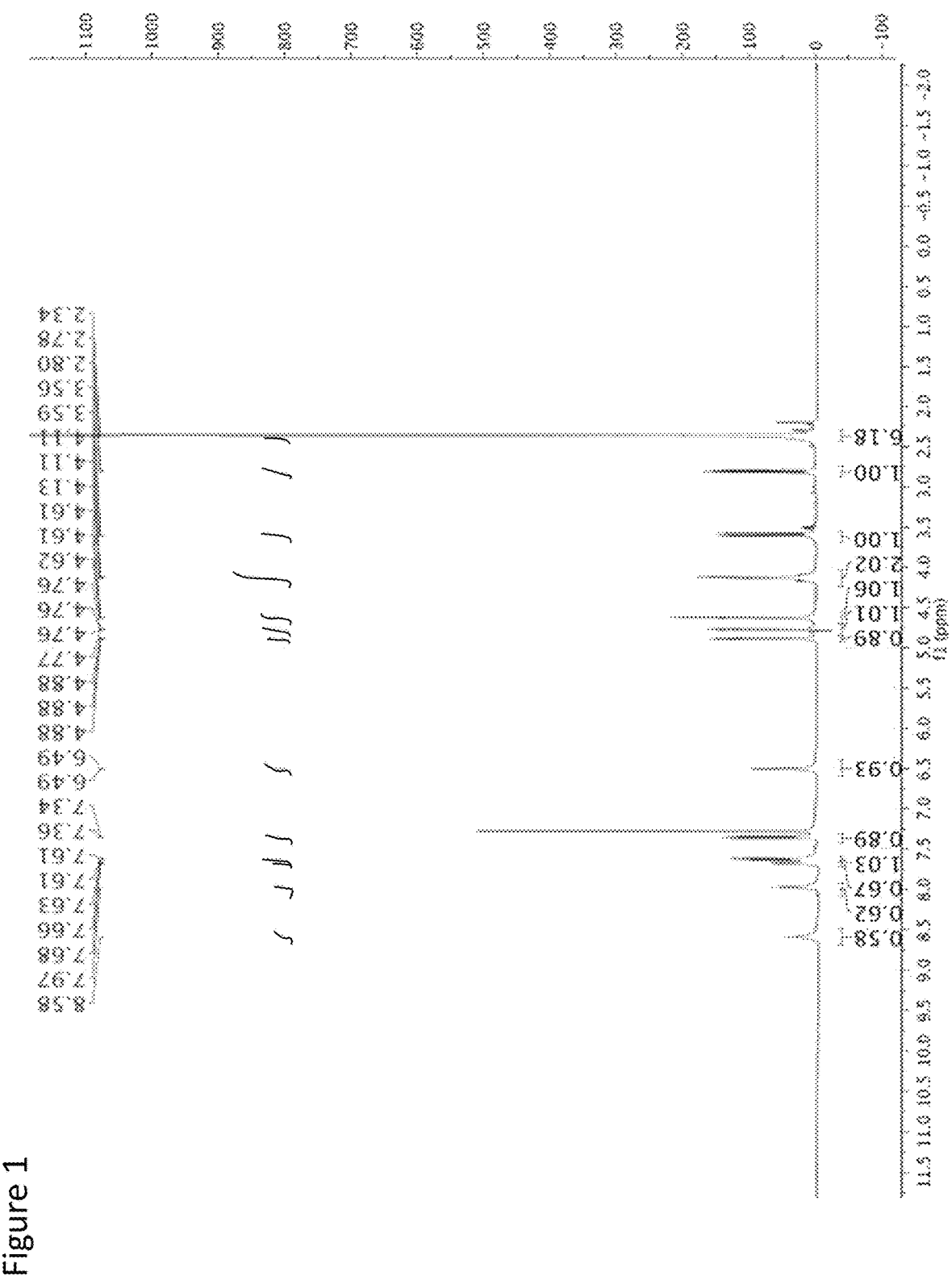
FIGS. 1 and 2 are NMR spectra of pure cymanquine (CMQ, 3) after chromatographic purification.

The present disclosure provides uses of CMQ and closely related compounds and derivatives thereof as anti-malaria agents. For example, the compounds can be used in methods of treating or preventing malaria. The terms "treatment" or "treating" are used herein to mean reducing the severity of malaria. This may entail ameliorating one or more symptoms associated with malaria.

The CMQ compounds used in the present methods comprise $CpMn(CO)_{3-n}L_n$ or $CpRe(CO)_{3-n}L_n$ moieties, where Cp is a cyclopentadienyl ligand and n=0, 1, or 2. The Cp group of the $CpMn(CO)_{3-n}L_n$ or $CpRe(CO)_{3-n}L_n$ moieties may be substituted (e.g., with an amine-substituted alkyl group). L is linked directly to the Mn. The Mn compounds can be referred to as cymantrene 'conjugates', which comprise cymantrene (cyclopentadienyl manganese tricarbonyl, $CpMn(CO)_3$, is called cymantrene) covalently bonded (i.e., conjugated to) a molecular moiety (i.e., a 'backbone') that has some biological relevance, e.g., a chloroquinoline moiety.

As used herein, the term "alkyl group," unless otherwise stated, refers to branched or unbranched hydrocarbons. Examples of such alkyl groups include methyl groups, ethyl groups, propyl groups, butyl groups, isopropyl groups, tert-butyl groups, and the like. For example, the alkyl group is a $C_1$ to $C_3$ alkyl group including all integer numbers of carbons and ranges of numbers of carbons therebetween. Alkyl groups may be substituted with various other functional groups. For example, the alkyl groups can be substituted with groups such as, for example, amines (acyclic and cyclic), alcohol groups, ether groups, and halogen atoms.

In one embodiment, the compound is compound, 5, which has a $CH_2NMe_2$ group in place of a hydrogen on the cyclopentadienyl ring. In one embodiment, the compound is the manganese derivative 3 or 4. The "pseudo-cymanquine" compound 4 lacks the cyclopentadienyl-$CH_2NMe_2$ group of CMQ.

The present disclosure provides compounds for use in a method for reducing or inhibiting the growth of organisms of the *Plasmodium* species, including, for example, *Plasmodium falciparum, Plasmodium vivax, Plasmodium ovale, Plasmodium malariae*, and/or *Plasmodium knowlesi*, in a medium or in an individual (including a human), where the compounds are provided and/or administered in a pharmaceutically acceptable carrier, and where the compounds have the following general structure:

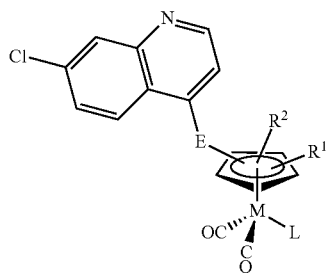

where M is Mn or Re. L is a neutral, two-electron donor (examples of suitable two-electron donors include —CO, phosphines (e.g., alkyl phosphines, aryl phosphines, alkyl aryl phosphines), phosphites (e.g., alkyl phosphites, aryl phosphites, alkyl aryl phosphites), aryl amines (e.g., pyridine and its analogues substituted by standard functionalities such as halide or alkyl groups at the ortho or para position), alkynes and carbenes. $R^1$ is H or an amine-substituted alkyl group, and $R^2$ is H, $(CH_2)_nCH_3$ (n=0, 1, 2 or higher. In one embodiment, n is an integer from 1 to 10), OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I.

$R^1$ can be —$(CH_2)_nNR^3R^4$, where n is 1 or higher, and $R^3$ and $R^4$ are independently H or a $C_1$-$C_x$ alkyl group, where x is 2 or higher). N can be any integer from 1 to 20 and x is any integer from 2 to 20. For example, n can be any integer from 1 to 10 and x is any integer from 2 to 10.

E can be a linker moiety connecting the cyclopentadienyl moiety with the chloroquinoline moiety. Examples of suitable linker moieties include —$NH(CH_2)_n$—, —$NH(CH_2)_n$NH— (where n is 1, 2 or higher. For example, n can be is any integer from 1 to 10, including all integer values and ranges therebetween), and —$NH(CH_2)_nNH$—$(CH_2)$— (where n is 1, 2 or higher. For example, n can be is any integer from 1 to 10, including all integer values and ranges therebetween).

L can be a water-soluble phosphine.

In an embodiment, the compounds do not have the following structure:

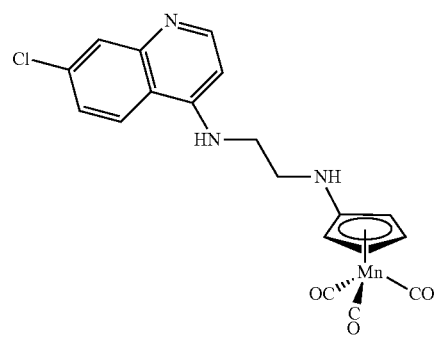

In different embodiments, the compound has the following structures:

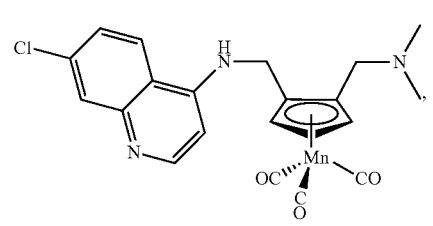

Cymanquine

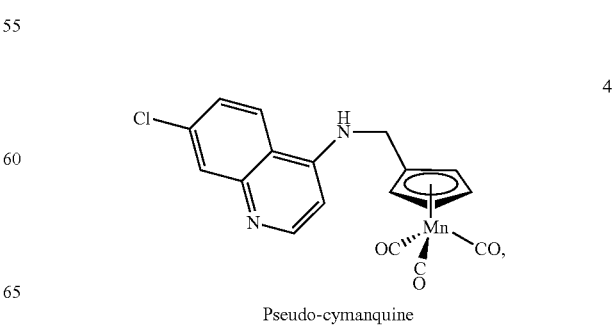

Pseudo-cymanquine

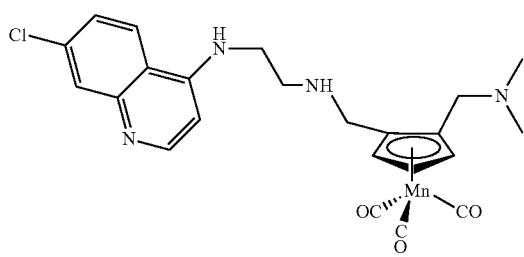

The present method includes the use of all possible stereoisomers and geometric isomers of all compounds. The present method also includes both racemic compounds and optically active isomers. When a compound is desired as a single enantiomer, it can be obtained either by resolution of the final product or by stereospecific synthesis from either isomerically pure starting material or use of a chiral auxiliary reagent. For example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of a compound are possible, the present disclosure is intended to include all tautomeric forms of the compounds.

The compounds of the present disclosure may be used as pharmaceutically acceptable salts. As used herein, the term "pharmaceutically acceptable salts" refers to salts or zwitterionic forms of the compound or compounds. In one embodiment, any type of salt may be used. Salts of the compound or compounds can be prepared during the final isolation and purification of the compounds or separately by reacting the compound with an acid having a suitable cation. The pharmaceutically acceptable salts of the compound or compounds are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, p-toluenesulfonate, and tetrakis(perfluorophenyl)borate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include the compounds as well as pharmaceutically acceptable salts, hydrates, or prodrugs thereof.

A diverse "tag toolbox" may be used to address the breadth of chemical, biological, and analytical needs. The $MCp(CO)_2L$ system (M=Mn, Re; L=CO or other two-electron ligand) offers desirable possibilities owing principally to its very strong, charge-sensitive, carbonyl IR absorptions, as well as a range of other spectroscopic possibilities. Compounds of the type $M(\eta^5\text{-}C_5H_4R)(CO)_2L$ are either commercially available or easily prepared. Here, $(\eta^5\text{-}C_5H_4R)$ refers to a Cp ring in which a hydrogen atom has been replaced by another atom or group R. These complexes have outstanding air- and thermal-stability, and undergo the types of chemistry at the five-membered ring that are known in the art to allow tagging and derivitization. A ligand L (e.g., a two-electron donor described herein) can be introduced to further modify the properties of the organometallic tag, for example by replacing a carbonyl with a donor ligand that modulates the oxidative redox potential or provides water-solubility for biological applications. For example, a second two-electron ligand, L or L', could be added, replacing another CO ligand. This further changes the physical and chemical properties of the complexes, but retains their strong infrared (IR) activity owing to the remaining CO ligand.

To enhance the solubility of the complexes in aqueous solutions, derivatives can be prepared in which a CO is replaced by a water-solubilizing phosphine ligand. The neutral form of the compound is slightly soluble in DMSO and in water. The hydrochloride salt is much more soluble in water. The compound could be stored at room temperature without noticeable degradation over a period of at least 6 months. For example, the compounds, or compositions comprising the compounds are stored protected from light, such as in the dark.

The compounds or a combination of the compounds can be used to reduce the growth of organisms of the *Plasmodium* species (such as, for example, *Plasmodium falciparum, Plasmodium vivax, Plasmodium ovale, Plasmodium malariae, Plasmodium knowlesi* and the like) treat or alleviate the symptoms of malaria, or to prevent or reduce the risk of developing malaria. In one embodiment, the present compounds are administered in a therapeutically effective amount.

The term "therapeutically effective amount" of a compound refers to an amount which is effective, upon single or multiple dose administration to an individual, for alleviating the symptoms of, or treating malaria. The exact amount desired or required will vary depending on the particular compound or composition used, its mode of administration and the like. Appropriate effective amount can be determined by one of ordinary skill in the art informed by the instant disclosure using only routine experimentation.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

Accordingly, the present disclosure further provides administration of pharmaceutical formulations comprising the compound or compounds, or a pharmaceutically acceptable salt, prodrug, or hydrate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

Compositions comprising a compound of the disclosure and a pharmaceutical agent for use in the present methods can be prepared at a patient's bedside, or by a pharmaceutical manufacture. In the latter case, the compositions can be provided in any suitable container, such as a sealed sterile vial or ampule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described can include one or more standard pharmaceutically acceptable carriers. Some examples herein of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art can be used to administer the compositions of the disclosure to an individual. For example, a compound or mixture of compounds, or compositions containing one or more compound, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intracranial, intradermal, subcutaneous, intraperitoneal, subcutaneous, intramuscular, intrathecal, and intraarticular. The compound(s) also can be administered in the form of an implant, which allows a slow release of the compound(s), as well as a slow controlled i.v. infusion.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The methods of the disclosure include administering to a subject a therapeutically effective amount of a compound or compounds in combination with another pharmaceutically active ingredient. Other pharmaceutically active ingredients that may be used can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell New Jersey, Medical Economics Co., *Formulary*, 2012; 252-256. A compound or compounds and the pharmaceutically active ingredient may be administered to the subject in the same pharmaceutical composition or in different pharmaceutical compositions (at the same time or at different times).

Methods disclosed herein include those where the subject is identified as in need of a particular stated treatment. Identifying a subject in need of such treatment can be in the judgment of a subject or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment.

The individual for administration of the present compounds and compositions may be human or may be a non-human animal. For veterinary use, a compound or compounds, or a pharmaceutically acceptable salt, is administered as a suitably acceptable formulation in accordance with normal veterinary practice. The veterinarian can readily determine the dosing regimen and route of administration that is most appropriate for a particular animal. Animals treatable by the present compounds and methods include birds, reptiles, and other animals.

The present compositions and compounds may be administered to an individual who has been diagnosed with malaria or to an individual who is at risk of developing malaria. For example, the compositions or compounds may be administered to an individual who may be at risk of developing malaria due to travel to high risk areas. Administration may continue as long as needed. For example, administration may continue until the individual is deemed to be malaria-free or until the individual is no longer at risk of developing malaria.

The present compounds and compositions may be useful for treatment against multiple *Plasmodium* species. In one embodiment, the *Plasmodium* species may be *Plasmodium falciparum*. In one embodiment, the *Plasmodium* species may be *Plasmodium vivax*. In one embodiment, the *Plasmodium* species may be *Plasmodium ovale*. In one embodiment, the *Plasmodium* species may be *Plasmodium malariae*. In one embodiment, the *Plasmodium* species may be *Plasmodium knowlesi*. In one embodiment, the *Plasmodium* may be a combination of various species.

In an aspect, the disclosure provides a packaged composition including a therapeutically effective amount of a compound or compounds and a pharmaceutically acceptable carrier or diluent. The compositions may be packaged with instructions to treat one or more individuals suffering from or at risk of developing malaria. Similarly, in one embodiment, kits may be provided which include a compound or compounds, pharmaceutically acceptable esters, and salts thereof, and instructions for use. The kits may be packaged such that they are useful as travel kits. For example, a dose for each administration may be packaged separately, such as in a blister wrap packaging.

In one aspect, this disclosure provides a method of treatment or prophylaxis of malaria comprising administering to an individual who has been diagnosed with, is suffering from, or is at risk of developing malaria comprising administering to the individual a therapeutically effective amount of a composition comprising one of more compounds of the following formula:

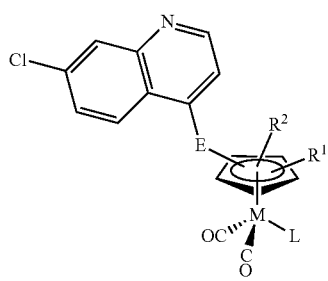

where: M is Mn or Re; L is a neutral, two-electron donor ligand; $R^1$ is H or an amine-substituted alkyl group; $R^2$ is H, $(CH_2)_nCH_3$, where n is 0 or any integer from 1 to 20, OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety. $R^1$ can be $(CH_2)_nNR^3R^4$, where n is an integer from 1 to 20 and $R^3$ and $R^4$ are independently H or an $C_1$-$C_x$ alkyl group, where x is an integer from 2 to 20. L can be —CO, phosphines (e.g., alkyl phosphines, aryl phosphines, or alkyl aryl phosphines), phosphites, aryl amines (e.g., pyridine), and carbenes. E can be —$NH(CH_2)_n$—, $NH(CH_2)_nNH$— where n is an integer from 1 to 10, or —$NH(CH_2)_nNH$—$(CH_2)$—, where n is an integer from 1 to 10. A second CO ligand can be replaced by a two-electron donor. M can be Mn and $R^1$ can be an amine substituted alkyl group. The compositions may be administered via any route, such as, for example, by oral or parenteral route. The compositions may be administered in multiple doses given one or more times a day over a period of one or more days.

In one embodiment, this disclosure provides a method for inhibiting the growth of organisms of the *Plasmodium* species, including, for example, *Plasmodium* falciparum, *Plasmodium* vivax, *Plasmodium* ovale, *Plasmodium* malariae, and/or *Plasmodium* knowlesi. The *Plasmodium* may be a combination of various species. The method comprises contacting the organisms with an effective amount of a composition comprising one of more compounds of the following formula:

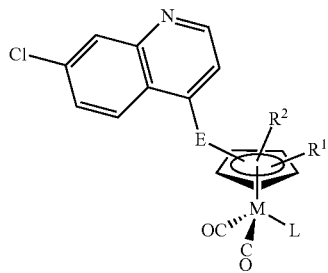

where: M is Mn or Re; L is a neutral, two-electron donor ligand; $R^1$ is H or an amine-substituted alkyl group; $R^2$ is H, $(CH_2)_nCH_3$, where n is 0 or any integer from 1 to 20, OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety. $R^1$ can be $(CH_2)_nNR^3R^4$, where n is an integer from 1 to 20 and $R^3$ and $R^4$ are independently H or an $C_1$-$C_x$ alkyl group, where x is an integer from 2 to 20. L can be —CO, phosphines (e.g., alkyl phosphines, aryl phosphines, or alkyl aryl phosphines), phosphites, aryl amines (e.g., pyridine), and carbenes. E can be —$NH(CH_2)_n$—, $NH(CH_2)_nNH$—, where n is an integer from 1 to 10, or —$NH(CH_2)_nNH$—$(CH_2)$—, where n is an integer from 1 to 10. A second CO ligand can be replaced by a two-electron donor. M can be Mn and $R^1$ can be an amine substituted alkyl group. The step of contacting the organisms may be carried out by contacting the medium in which these organisms are growing with the present compositions comprising an effective amount of the present compounds, or may be carried out by administering to an individual who is suspected of having or harboring these organisms or who is at risk of coming into contact with these organisms, a therapeutically effective amount of the present compounds. If administered to an individual, the compositions may be administered via any route, such as, for example, by oral or parenteral route. The compositions may be administered in multiple doses given one or more times a day over a period of one or more days.

For example, the method of inhibiting the growth of organisms of the *Plasmodium* species, or of treating or preventing malaria comprises administering to an individual in need of treatment a composition comprising one or more of the following compounds:

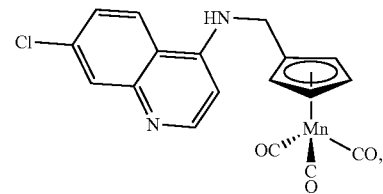

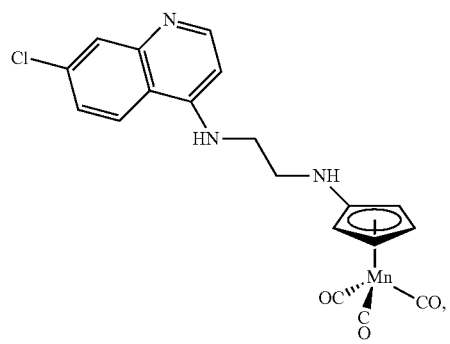

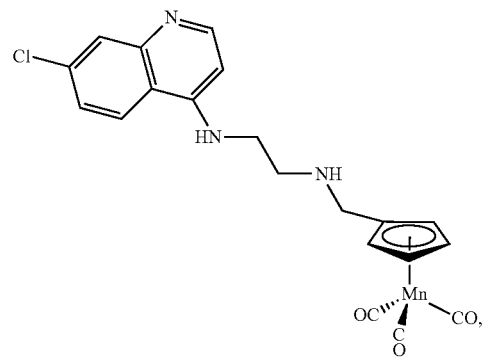

-continued

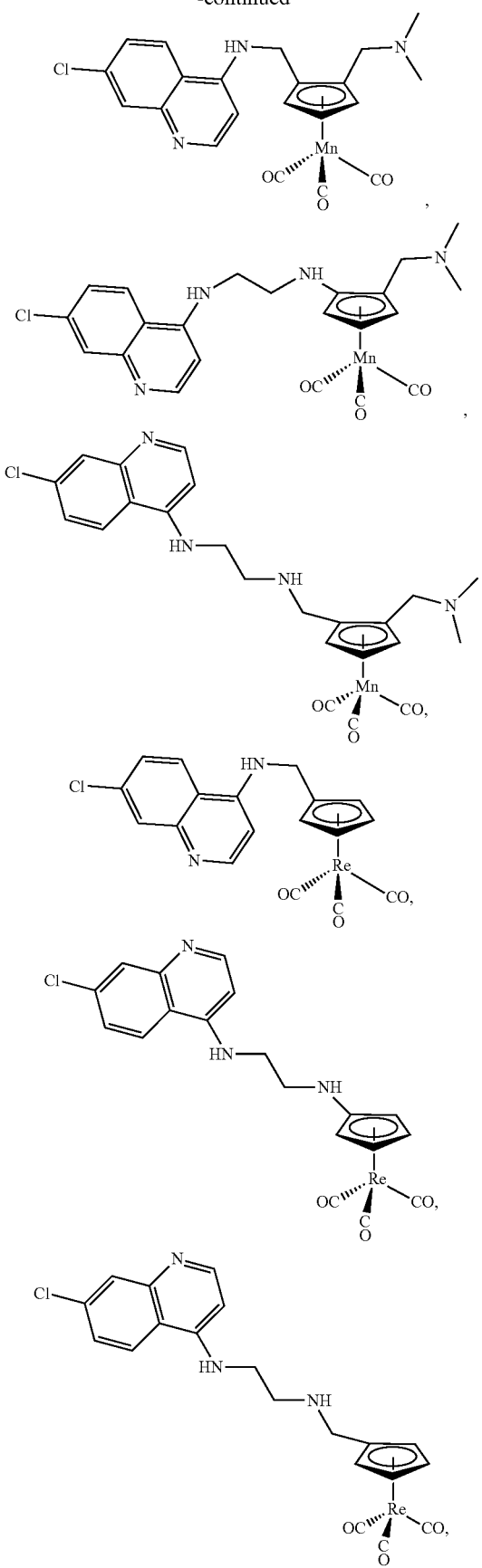

-continued

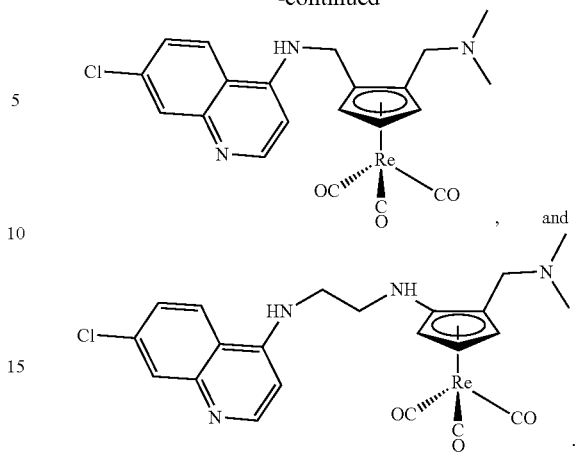

The following examples further describe the disclosure. These examples are intended to be illustrative and not limiting in any way.

Example 1

The following is an example of the synthesis of CMQ and derivatives thereof.

Preparation of CMQ, 3 (Mixture of 2 Isomers).

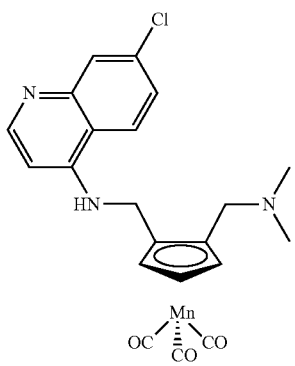

α-Formyl-(N,N-dimethylaminomethyl)cymantrene was synthetized following a known procedure: Loim, N. M., Abramowa, N. A., Parnes, Z. N., Kursanow, D. N., *J. Organomet. Chem.*, 1979, 168, $C_{33}$.

α-Formyl-(N,N-dimethylaminomethyl)cymantrene (1.12 g, 3.87 mmol, 1 eq) was dissolved in 40 mL of dry methanol at 0° C. Then, sodium borohydride (0.322 g, 8.52 mmol, 2.2 eq) was added by portion over 15 minutes and the solution was allowed to come back to room temperature. After 2 hours, most of the solvent was removed under reduced pressure and the mixture was dissolved in 30 mL of dichloromethane. The organic solution was washed twice with 30 mL of water, after which the organic layer was isolated, dried over magnesium sulfate, filtered, and the solvent removed under reduced pressure. α-hydroxymethyl-(N,N-dimethylaminomethyl)cymantrene was obtained in a 67% yield as dark brown oil and was pure enough to be used as it was in the next step.

To a solution of α-hydroxymethyl-(N,N-dimethylaminomethyl)cymantrene (50 mg, 0.172 mmol, 1 eq) in 1 mL of dry THF, were added phthalimide (32.3 mg, 0.22 mmol, 1.28 eq) and triphenylphosphine (57.6 mg, 0.22 mmol, 1.28 eq). Then diisopropyl diazene-1,2-dicarboxylate (DIAD) (47 uL, 0.22 mmol, 1.28 eq) was added. After an hour, the solvent was removed and replaced by 0.5 mL of methanol. Then hydrazine hydrate (24 uL, 0.32 mmol, 1.82 eq) was added and the solution was stirred at room temperature for 30 minutes. 10 mL of a 1N solution of HCl was added and the solution was extracted three times with 10 mL of ethyl acetate. The pH of the aqueous layer was then increased to 13 by addition of a solution of 1N NaOH and extracted three times with 10 mL of dichloromethane. The organic layers were combined, dried over magnesium sulfate, and the solvent removed under pressure to yield the desired α-aminomethyl-(N,N-dimethylaminomethyl)cymantrene which was used as it was in the next step. (26.2 mg).

Figure 2:
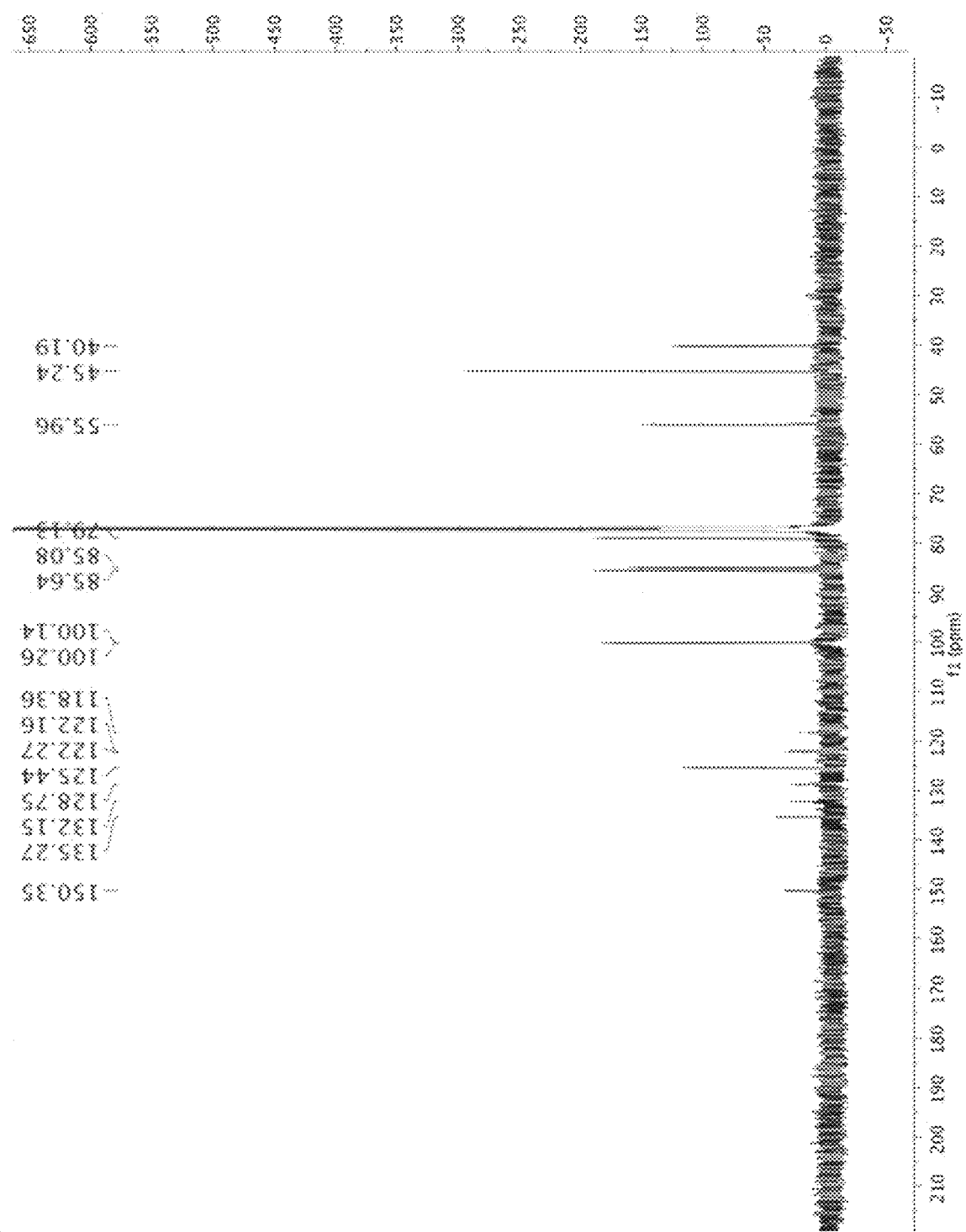

The crude α-aminomethyl-(N,N-dimethylaminomethyl) cymantrene (26.2 mg, 0.090 mmol, 1 eq) was dissolved in 2 mL of dry and degassed propanol and 7-chloro-4-fluoroquinoline (17.2 mg, 0.095 mmol, 1.05 eq). The solution was refluxed under nitrogen overnight, after which the solvent was removed under reduced pressure and the compound purified by column chromatography over silica gel using 1:9 ethyl acetate:hexanes as the eluent. A light brown powder was obtained (16% yield over 3 steps). See FIGS. 1 and 2 for NMR spectra.

$^1$H NMR (500 MHz, CDCl$_3$): 2.34 (s, 6H), 2.79 (d, J=12.9 Hz, 1H), 3.58 (d, J=12.9 Hz, 2H), 4.08-4.16 (m, 2H), 4.61 (t, J=2.75 Hz, 1H), 4.76-4.77 (m, 1H), 4.88 (m, 1H), 6.40 (s, 1H), 7.35 (d, J=8.9 Hz, 1H), 7.62 (d, J=8.9 Hz, 1H), 7.66-7.68 (m, 1H), 7.97 (s, 1H), 8.58 (s, 1H).

$^{13}$C NMR (500 MHz, CDCl$_3$): 40.2, 45.2, 56.0, 79.1, 85.1, 85.7, 100.1, 100.3, 118.4, 122.2, 122.3, 125.5, 128.7, 132.1, 135.3, 150.3 MSCI+ m/z (%): 455.1 (8), 454.1 (30), 453.2 (24), 452.2 (100), 418.2 (2), 274.1 (2), 54.8 (3)

IR (neat) umax/cm$^{-1}$: 632, 668, 807, 840, 1135, 1426, 1577, 1913, 1939, 2011, 2831, 2950

Anal. Calcd for C$_{21}$H$_{19}$ClMnN$_3$O$_3$: C, 55.83; H, 4.24; N, 9.30. Found: C, 56.25; H, 4.34; N, 9.43.

Preparation of Pseudo-Cymanquine, 4.

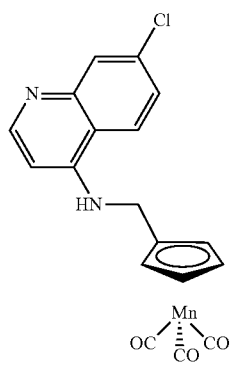

Aminomethylcymantrene was prepared following a known procedure: Telegina, L. N., Ezernitskaya, M. G., Godovikov, I. A., Babievskii, K. K., Loshin, B. V., Strelkova, T. V., Borisov, Y. A., Loim, N. M., *Eur. J. Inorg. Chem.*, 2009, 3636.

Figure 3:
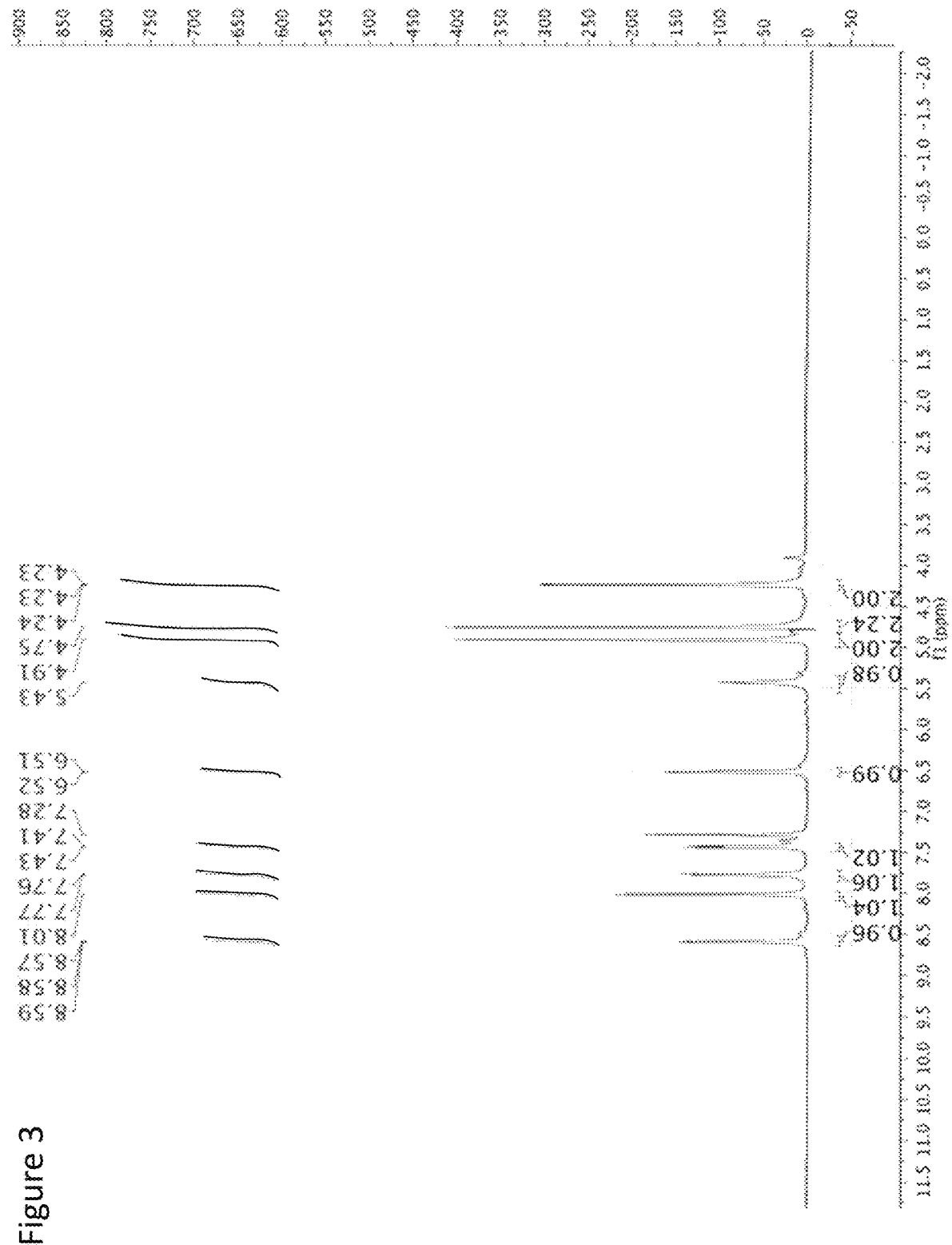
FIGS. 3 and 4 are NMR spectra of pure "pseudo"-cymanquine (4) after chromatographic purification.
Figure 4:
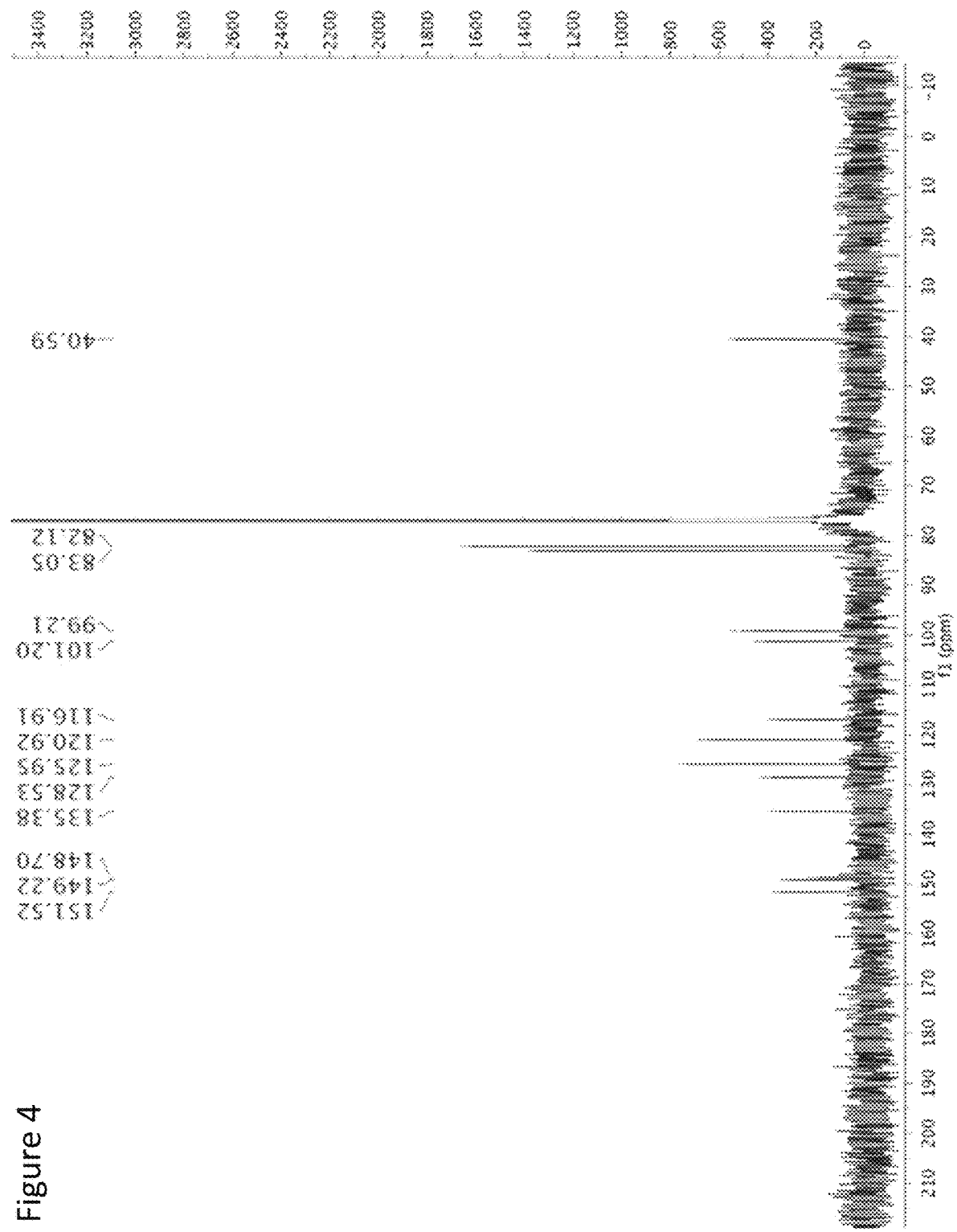

Aminomethylcymantrene (100 mg, 0.429 mmol, 1 eq) was dissolved in 5 mL of dry and degassed propanol and 7-chloro-4-fluoroquinoline (82 mg, 0.450 mmol, 1.05 eq). The solution was refluxed under nitrogen overnight after which the solvent was removed under reduced pressure and the compound purified by column chromatography over silica gel using 1:9 ethyl acetate:hexanes as the eluent. A light brown powder was obtained (67% yield). See FIGS. 3 and 4 for NMR spectra.

$^1$H NMR (500 MHz, CDCl$_3$): 4.23 (s, 2H), 4.75 (s, 2H), 4.91 (s, 2H), 5.43 (s, 1H), 6.51-652 (m, 1H), 7.42 (d, J=8.9 Hz, 1H), 7.77 (d, J=8.9 Hz, 1H), 8.01 (s, 1H), 8.57-8.59 (m, 1H)

$^{13}$C NMR (500 MHz, CDCl$_3$): 40.6, 82.1, 83.0, 99.2, 101.2, 116.9, 120.9, 125.9, 128.5, 135.4, 148.7, 149.2, 151.5.

MSCI+ m/z (%): 397.8 (3), 396.8 (15), 395.9 (8), 394.8 (42), 346.8 (14), 297.0 (14), 254.9 (5), 224.9 (13), 224.0 (22), 223.0 (100).

IR (neat) υ$_{max}$/cm$^{-1}$: 630, 664, 848, 1139, 1567, 1569, 1883, 1901, 1927, 2010.

Anal. Calcd for C$_{18}$H$_{12}$ClMnN$_2$O$_3$: C, 54.78; H, 3.06; N, 7.10 Found: C, 55.35; H, 3.11; N, 7.11.

Preparation of 5

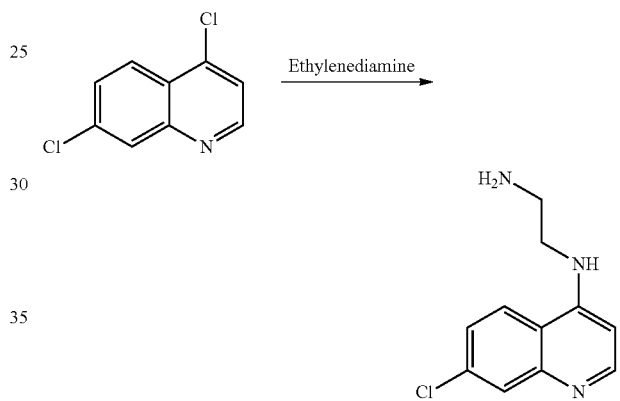

Dichloroquinoline (2 g, 10.10 mmol, 1 eq) was reacted with ethylenediamine (3.4 ml, 50.5 mmol, 5 eq) in 100 ml of xylene. The reaction mixture was refluxed overnight and then allowed to come back to room temperature. Most of the solvent was removed under reduced pressure and the mixture was dissolved in 30 mL of dichloromethane. The organic solution was washed twice with 30 mL of water, then the organic layer was isolated, dried over magnesium sulfate, filtered and the solvent removed under reduced pressure, yielding quantitatively the pure N1-(7-chloroquinolin-4-yl)ethane-1,2-diamine.

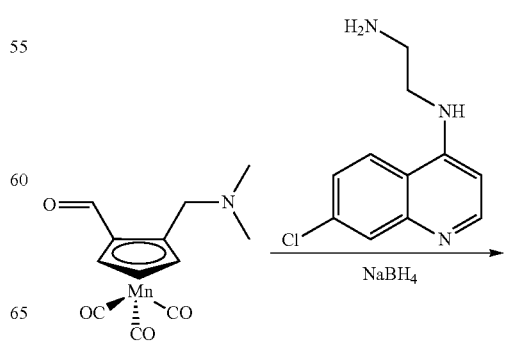

-continued

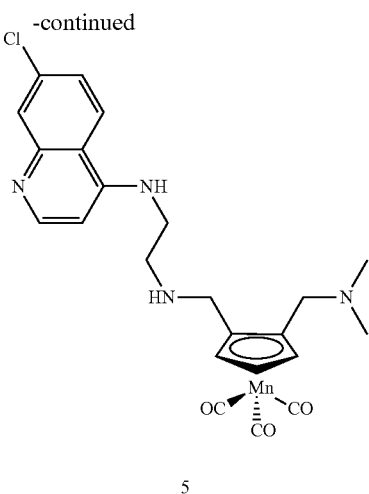

5

α-Formyl-(N,N-dimethylaminomethyl)cymantrene (0.1 g, 0.346 mmol, 1 eq) and N1-(7-chloroquinolin-4-yl)ethane-1,2-diamine (0.084 g, 0.380 mmol, 1.1 eq) were dissolved in 4 mL of dry methanol. The solution was refluxed for five hours and then cooled down to 0° C. Sodium borohydride (0.088 g, 0.414 mmol, 1.2 eq) was added by portion over 15 minutes and the solution was allowed to come back to room temperature. After 2 hours, most of the solvent was removed under reduced pressure and the mixture was dissolved in 5 mL of dichloromethane. This solution was washed twice with 5 mL of water, after which the organic layer was isolated, dried over magnesium sulfate, filtered and the solvent removed under reduced pressure. Compound 5 was obtained in a 59% yield as yellowish solid and was pure enough to be used as it was. An analytically pure sample could be obtained by a quick filtration over silica gel using 1:9 ethyl acetate:hexanes as the eluent.

Preparation of 6

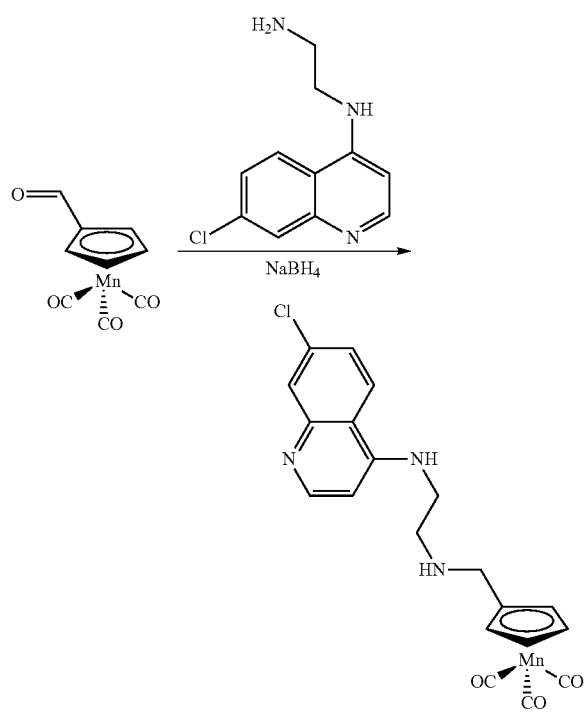

6

Compound 6 was prepared in a similar manner as 5 but by using formylcymantrene instead of α-Formyl-(N,N-dimethylaminomethyl)cymantrene.

Example 2

The following is an example of the characterization of CMQ and derivatives thereof.

Anodic Electrochemistry of CMQ Family. The electrochemical behavior of the three manganese compounds shown below was studied.

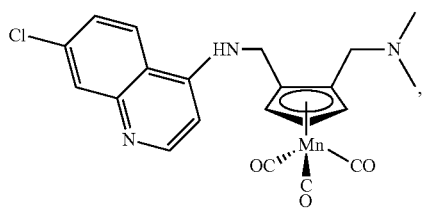

Cymanquine

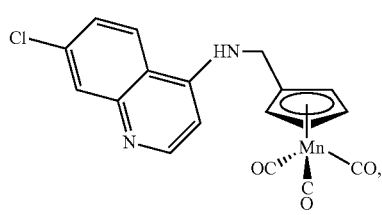

Pseudo-cymanquine

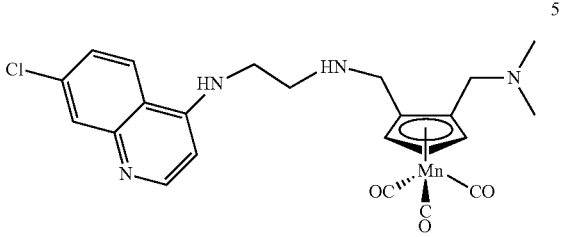

Electrochemical studies were carried out. The electrolyte solution used for these studies, namely dichloromethane with 0.05 M [NBu$_4$][B(C$_6$F$_5$)$_4$] as the supporting electrolyte, is known to provide an optimum medium for the electrochemical oxidation of compounds containing the MnCp (CO)$_3$ (Cp=η$^5$-C$_5$H$_5$) backbone (Laws et al., *J. Am. Chem. Soc.* 2008, 130, 9859). The potentials given here are referred to the ferrocene/ferrocenium reference couple. The experiments were carried out in a controlled atmosphere which minimizes exposure to oxygen and water. We refer to two types of standard electrochemical techniques that are commonly described in books on electrochemistry: cyclic voltammetry and bulk electrolysis (Bard, A. J.; Faulkner, L. R. *Electrochemical Methods*, John Wiley & Sons, New York, 2001, second edition) The former is useful for the analytical and gross mechanistic aspects of the electron-transfer properties of a compound, whereas the latter is most often employed for the electro-synthetic function of making isolable quantities of electrochemical oxidation or reduction products.

Anodic oxidation of the three compounds was investigated. They shared the basic character of having two consecutive one-electron oxidation processes, at the potentials given in the table. In each case, the first oxidation, at the potential $E_p(1)$, was a chemically irreversible one-electron process [$E_p$ refers to the peak potential of the voltammetric wave]. This means that the first one-electron oxidation product, e.g., 3⁺, reacted rapidly to give a new compound, referred to here as the "follow-up" product, that is responsible for the second oxidation process at the potential $E(2)$. The follow-up product was identified as having a structure in which the ring-nitrogen of the chloroquine moiety was protonated. This is shown below for CMQ as 3H⁺.

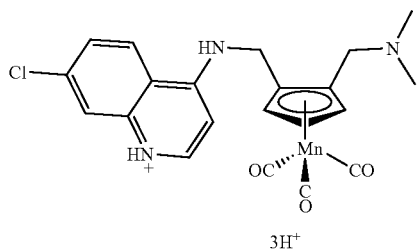

3H⁺

The quinoline-protonated product is apparently formed by a reaction in which the initially formed radical cation, e.g., 3+, abstracts a hydrogen atom from the solvent. In all three systems, the potential $E_p(1)$ is at a value expected for the oxidation of the chloroquine moiety, and the second oxidation, $E(2)$, is at a potential consistent with the one-electron oxidation of the cymantryl moiety, i.e., the MnCp(CO)₃ part of the molecule.

In the case of compound 4, the cyclic voltammograms show that the doubly-oxidized compound is persistent over the lifetime of the scan, which is of the order of 5-10 sec under our conditions. Thus, the oxidative electron-transfer reactions of 4 follow Eq 1, where SH=solvent:

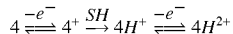

(1)

This oxidation mechanism was confirmed by bulk anodic electrolysis of 4, bulk cathodic electrolysis of 4H⁺ (which regenerated 4 by electron-induced deprotonation of 4H⁺), and by acid/base studies. For compound 3, the first oxidation again involved protonation of the quinoline-ring nitrogen in a follow-up reaction. The protonated product 3H⁺ was isolated and its structure confirmed by NMR spectroscopy. In the case of both 3 and 5, the second oxidation was chemically irreversible, and the follow-up products of the second oxidations have not yet been identified. Equation 2 gives the known aspects of the anodic oxidation of 3.

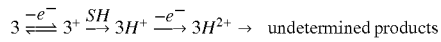

(2)

Table of potentials (vs ferrocene/ferrocenium (FcH)) measured by cyclic voltammetry for oxidation of compounds 3, 4, and 5 in dichloromethane/0.05 M [NBu₄][B(C₆F₅)₄]. $E_{1/2}$ is given for a chemically reversible process and the anodic peak potential, $E_p$, is given for an irreversible process.

| Compound | $E_p(1)$ (V vs FcH) | $E_{1/2}(2)$ or $E_p(2)$ (V vs FcH) | Comments |
|---|---|---|---|
| 3 | 0.82 | 1.25 ($E_p$) | |
| 4 | 1.14 | 1.35 ($E_{1/2}$) | 2$^{nd}$ oxdn partly reversible |
| 5 | 0.80 | 1.0 ($E_p$) | |

Figure 5:
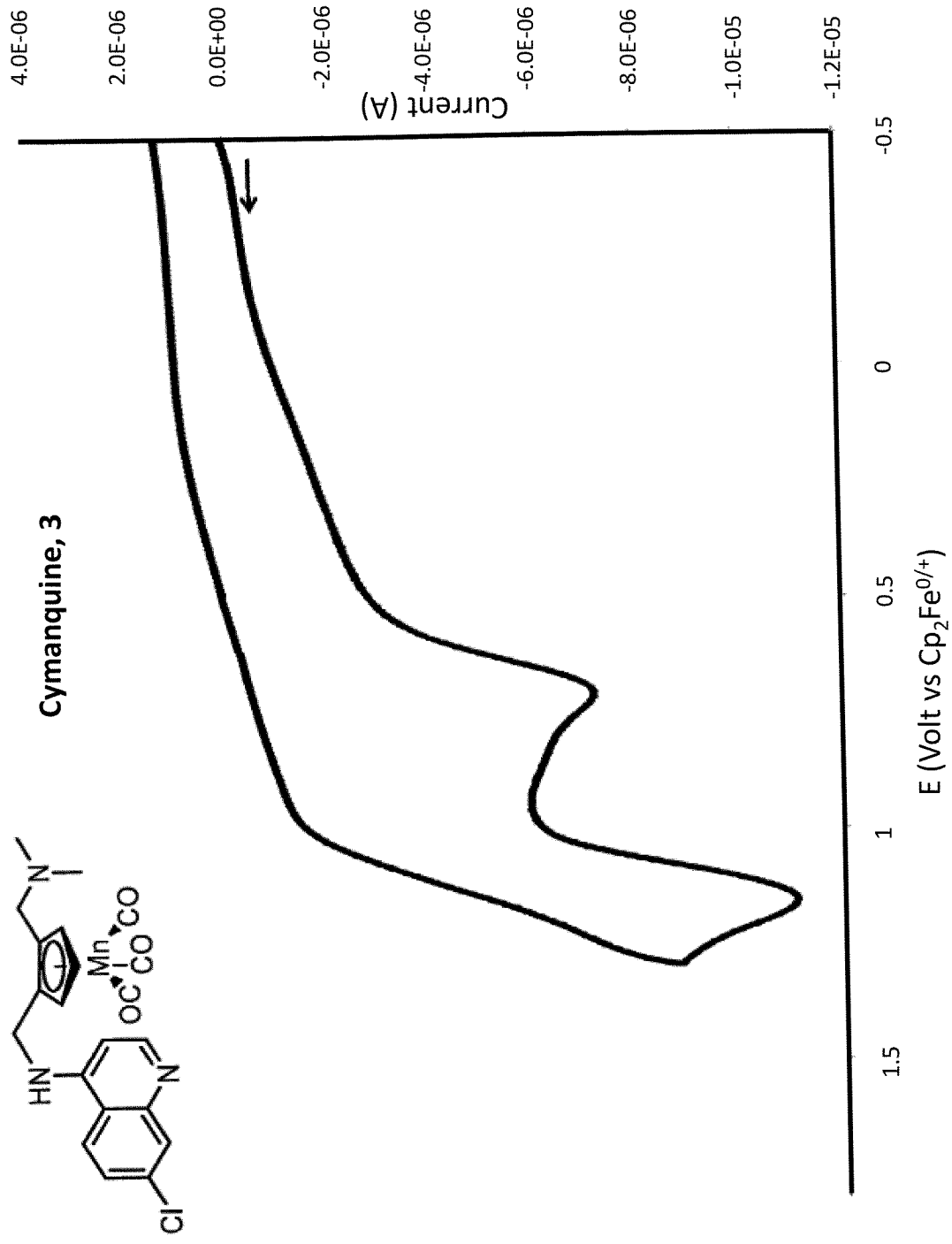
FIG. 5: Cyclic voltammetry scan recorded at a glassy carbon electrode for a solution of CMQ, 3, in dichloromethane containing 0.05 M [$NBu_4$][$B(C_6F_5)_4$] as supporting electrolyte.
Figure 6:
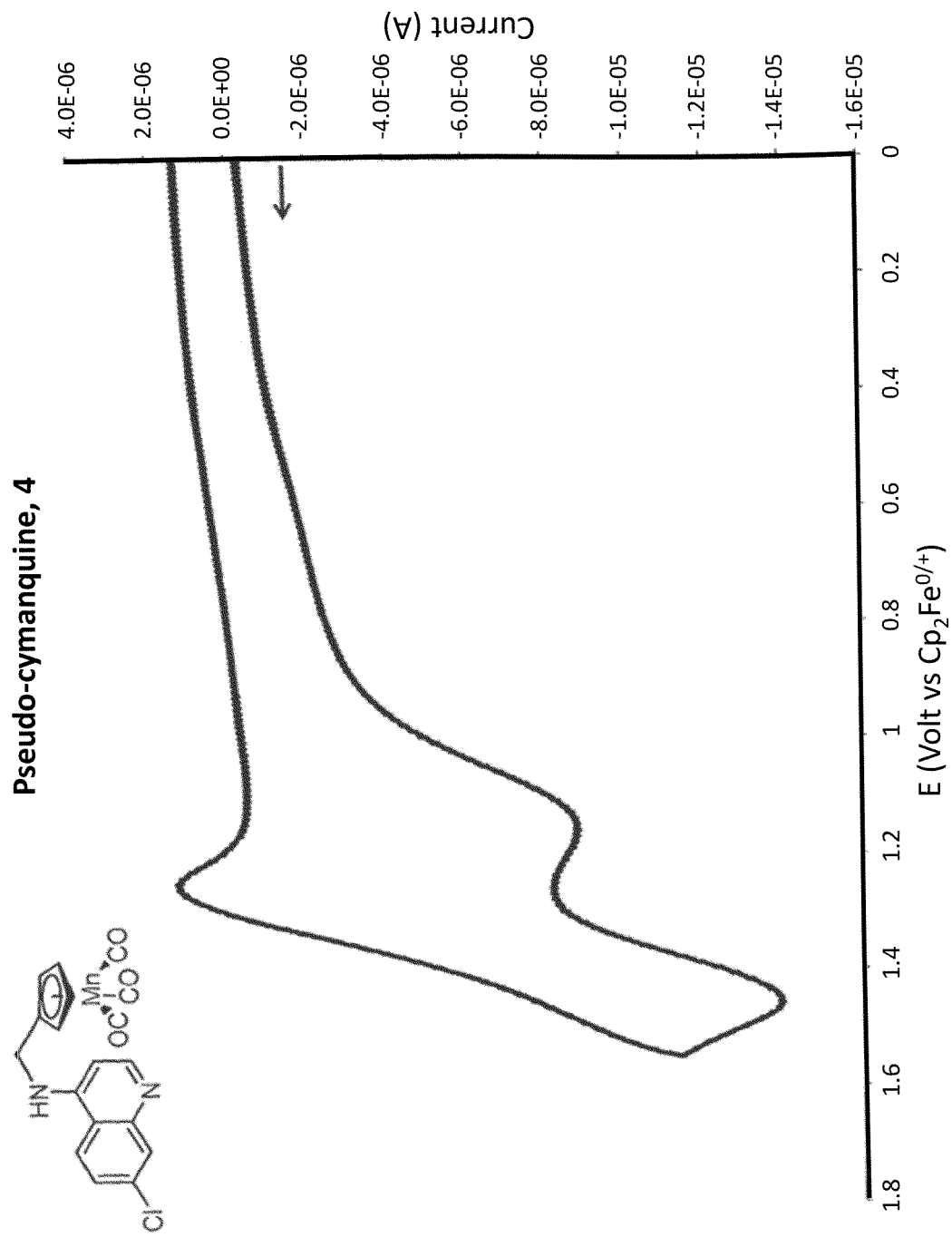
FIG. 6: Cyclic voltammetry scan recorded at a glassy carbon electrode for a solution of pseudo-cymanquine, 4, in dichloromethane containing 0.05 M [$NBu_4$][$B(C_6F_5)_4$] as supporting electrolyte.
Figure 7:
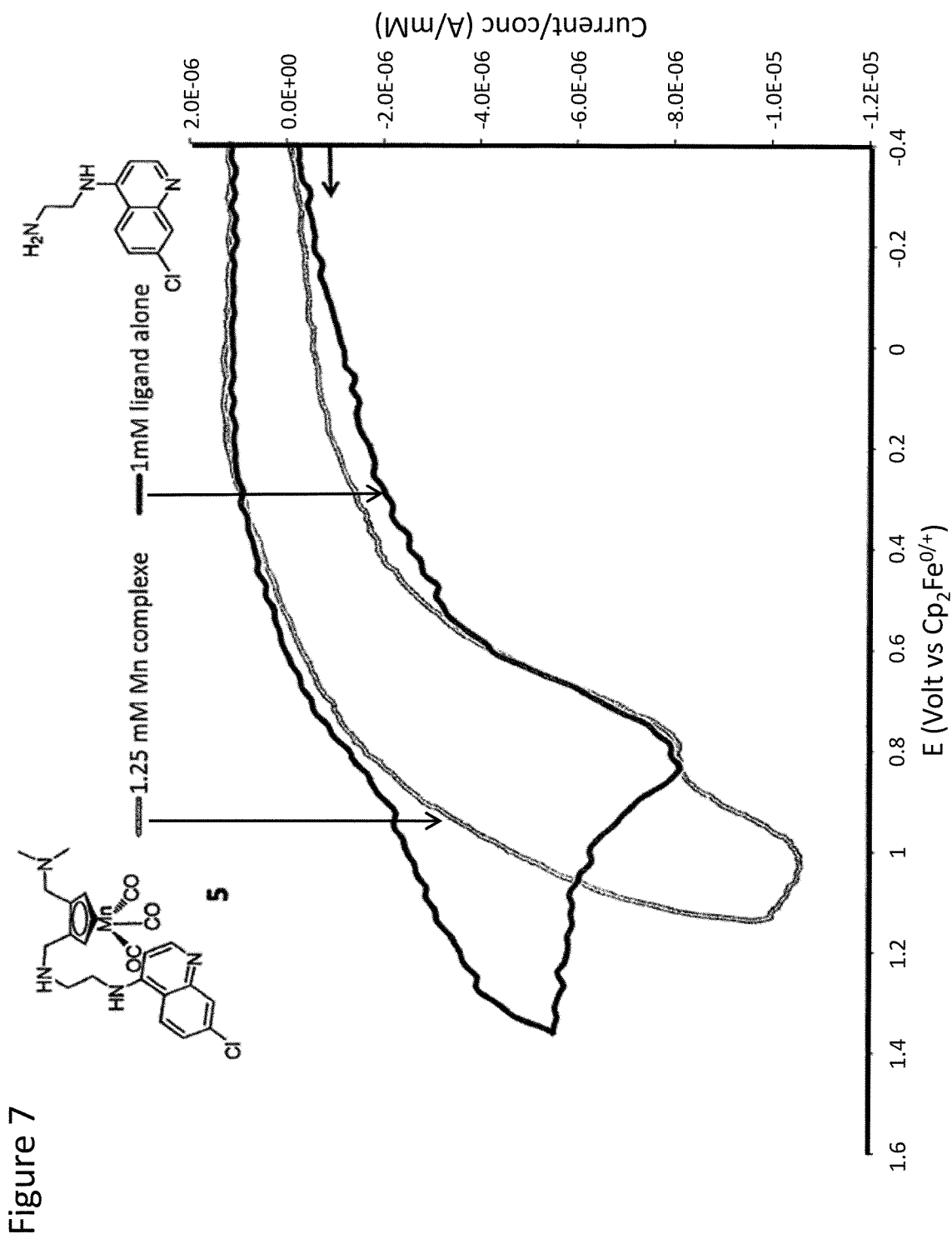
FIG. 7: Superposition of cyclic voltammetry scans recorded at a glassy carbon electrode for solutions of either the manganese compound 5, or the chloroquine-like "free ligand" in dichloromethane containing 0.05 M [$NBu_4$][$B(C_6F_5)_4$] as supporting electrolyte.

The electrochemical results demonstrate that the "cymanquine" family of compounds may be converted to proton-reactive species when they are exposed to positive potentials in the electrolyte medium. Standard electroanalytical methodologies may be employed, using simple carbon electrodes, for quantitative analysis of the compounds. These would include, but not be limited to, cyclic voltammetry (FIGS. 5, 6, and 7), square wave voltammetry, differential pulse voltammetry, and stripping voltammetry.

Example 3

The following is an example of a use of CMQ and derivatives thereof.

Figure 8:
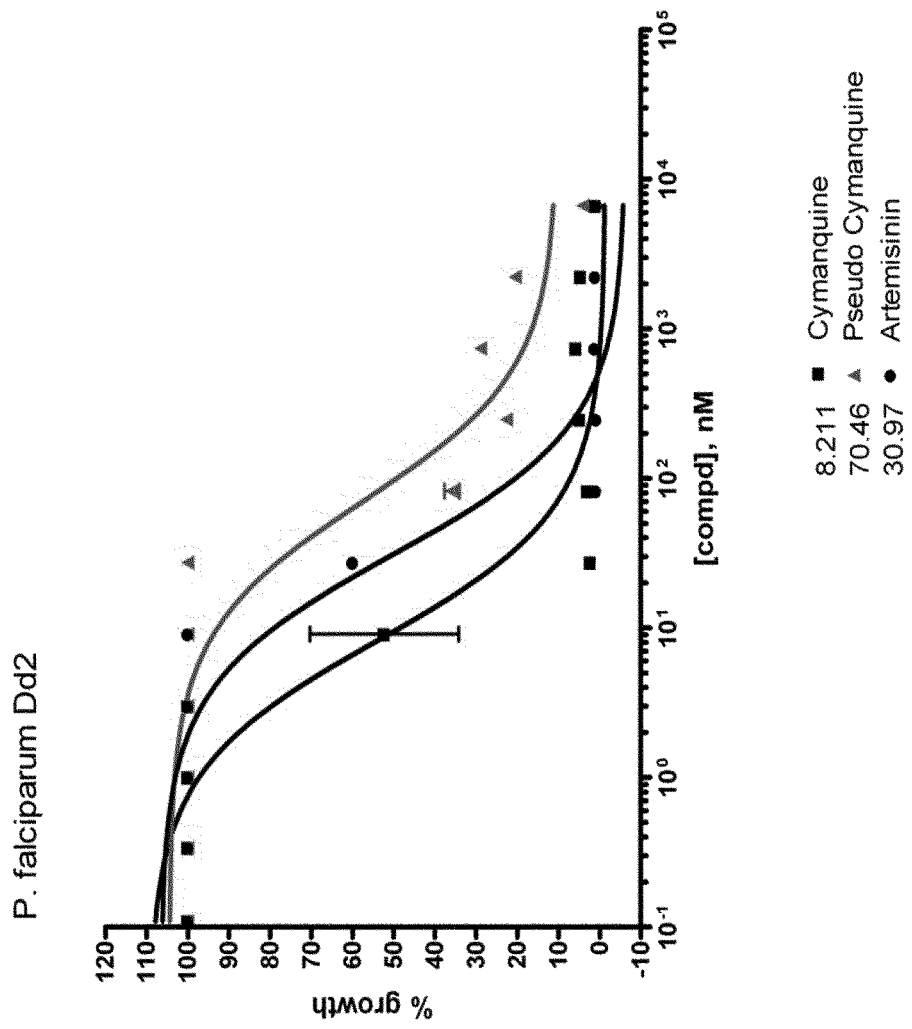
FIG. 8: EC50 for cymanquine, pseudocymanquine and artemisinin in *P. falciparum* strain Dd2.
Figure 9:
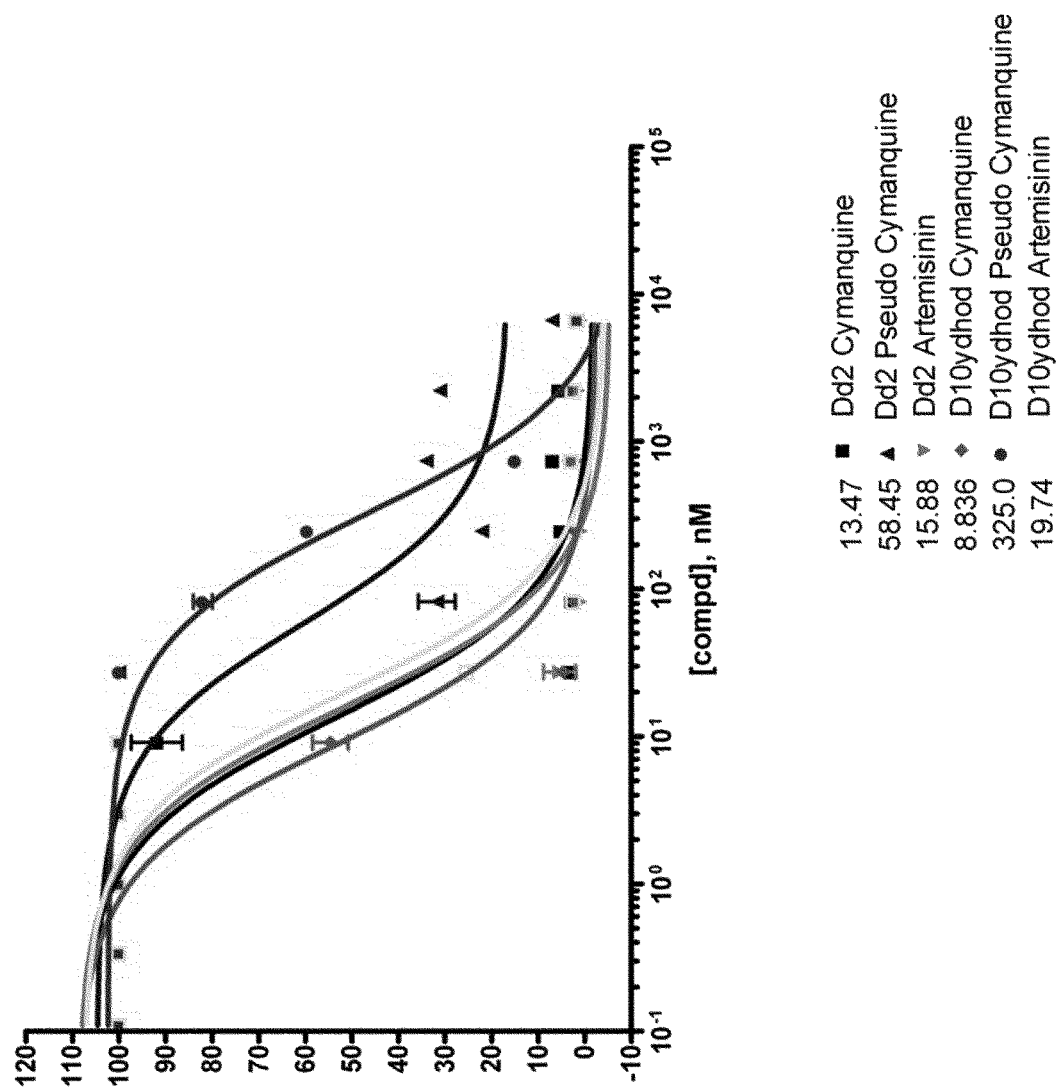
FIG. 9: EC50 for cymanquine, pseudocymanquine and artemisinin in *P. falciparum* strain Dd2 and strain $D10_{ydhod}$.

*P. falciparum* strains were cultured under standard conditions in RPMI1640 medium supplemented with 0.5% Albumax in 90% N2, 5% O2 and 5% $CO_2$. A modified version of the [³H]-hypoxanthine incorporation method was employed for assessing growth inhibition by the inhibitor compounds. Briefly, *P. falciparum* strain Dd2 or strain D10$_{ydhod}$ (this strain express the *Saccharomyces cerevisiae* dihydroorotate dehydrogenase enzyme which renders mitochondrial electron transport nonessential in the parasite) parasites were seeded at 2% parasitemia in 96-well plates and treated with varying concentration of the inhibitors as well as the solvent (DMSO) for 24 h. [³H]-Hypoxanthine was added to the cultures and incubation was continued for an additional 24 h. Incorporation of [³H]-hypoxanthine by the parasites was determined by liquid scintillation. Growth inhibition was assessed as decrease in [³H]-hypoxanthine incorporation in treated parasites relative to the control parasites treated with the solvent. The dose-response data were analyzed using nonlinear regression analysis (Prism GraphPad), and the EC50 was derived using an inhibitory sigmoid maximum effect ($E_{max}$) model. Each assay is completed in triplicate and the average EC50 was calculated. The results seen in FIGS. 8 and 9 indicate that Cymanquine has EC50 of approximately 10.8 nM vs. the multidrug resistant parasite strain Dd2, which is nearly equivalent if not slightly more potent than the known anti-malarial artemisinin. Equivalent potency is observed against parasite strain D10$_{ydhod}$. Pseudo-Cymanquine is slightly less potent with an EC50 of approximately 64.4 nM against strain Dd2. The EC50 against parasite strain D10$_{ydhod}$ is approximately 5-fold higher suggesting some involvement of the parasite electron transport chain. It should be noted that the EC50 of atovaquone, a known parasite electron transport inhibitor is >2000-fold higher in strain D10$_{ydhod}$ as compared to the parental D10 parasite. These results indicate that both compounds show potent antimalarial activity, including activity against a multidrug resistant parasite strain. These compounds demonstrate excellent potential for antimalarial use.

While the disclosure has been described through illustrative examples, routine modifications of the various embodiments will be apparent to those skilled in the art and such modifications are intended to be within the scope of this disclosure.

What is claimed is:

1. A method of treatment of malaria comprising administering to an individual who has been diagnosed with and/or is suffering from malaria comprising administering to the individual a therapeutically effective amount of a composition comprising one of more compounds of the following formula:

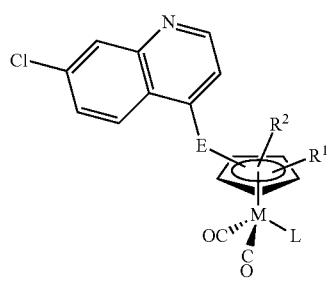

wherein:

M is Mn or Re,

L is a neutral, two-electron donor ligand,

R¹ is an amine-substituted alkyl group,

R² is H, (CH₂)ₙCH₃, wherein n is 0 or any integer from 1 to 20, OMe, OEt, OPh, Ph, CHO, COMe, COPh, CH₂OH, CO₂H, CO₂Me, CO₂Et, CH₂Ph, NH₂, NMe₂, NEt₂, C₆H₄Me, C₆H₄OMe, NH₂COMe, F, Cl, Br, or I; and E is a linker moiety connecting the cyclopentadienyl moiety with the chloroquinoline moiety, wherein E is —NH(CH₂)ₙ—, —NH(CH₂)ₙNH—, or —NH(CH₂)ₙNH(CH₂)— and n is an integer from 1 to 10.

2. The method of claim 1, wherein R¹ is (CH₂)ₙNR³R⁴, wherein n is an integer from 1 to 20 and R³ and R⁴ are independently H or an C₁-Cₓ alkyl group, wherein x is an integer from 2 to 20.

3. The method of claim 1, wherein L is —CO, a phosphine, a phosphite, an aryl amine, or a carbene.

4. The method of claim 3, wherein the phosphine is a water-soluble phosphine.

5. The method of claim 3, wherein the phosphine is alkyl phosphine, aryl phosphine, or alkyl aryl phosphine.

6. The method of claim 3, wherein the aryl amine is pyridine.

7. The method of claim 1, wherein a second CO ligand is replaced by a two-electron donor.

8. The method of claim 1, wherein M is Mn.

9. The method of claim 1, wherein the compound has the following structure:

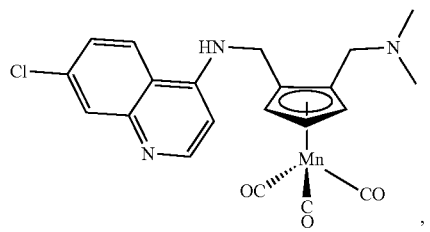

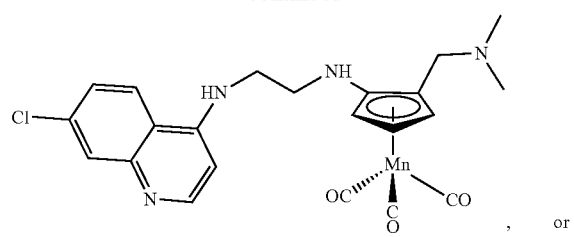

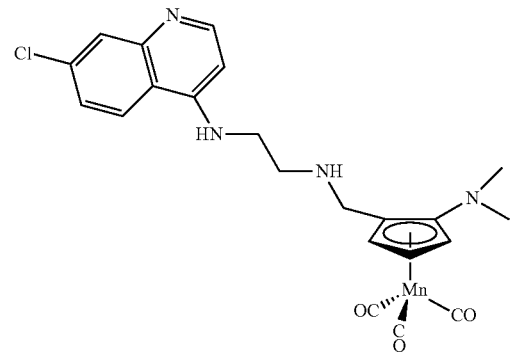

10. The method of claim 1, wherein the compound has the following structure:

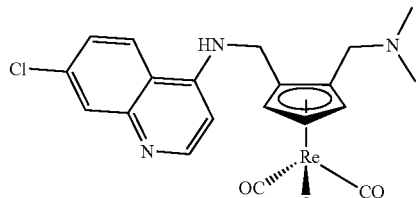

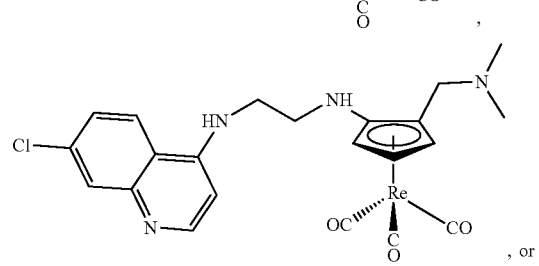

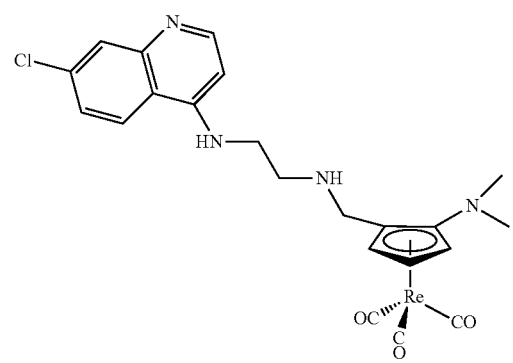

11. The method of claim 3, wherein M is Mn.

12. A kit comprising one or more containers or packaging having a compound of claim 1, and instructions for use for treatment of malaria.

13. The kit of claim 12, wherein the kit comprises a plurality of individualized sealed packets, each individual packet representing a dose of the composition for a single use.

* * * * *

UNITED STATES PATENT AND TRADEMARK OFFICE
CERTIFICATE OF CORRECTION

PATENT NO. : 10,512,652 B2
APPLICATION NO. : 15/745938
DATED : December 24, 2019
INVENTOR(S) : William E. Geiger, Kevin Lam and Lawrence W. Bergman Page 1 of 1

It is certified that error appears in the above-identified patent and that said Letters Patent is hereby corrected as shown below:

In the Claims

Column 20, Lines 11-24, in Claim 9, the third structure should read:

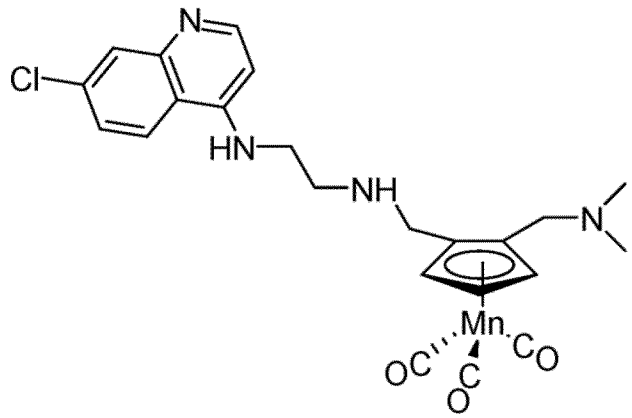

Column 20, Lines 48-61, in Claim 10, the third structure should read:

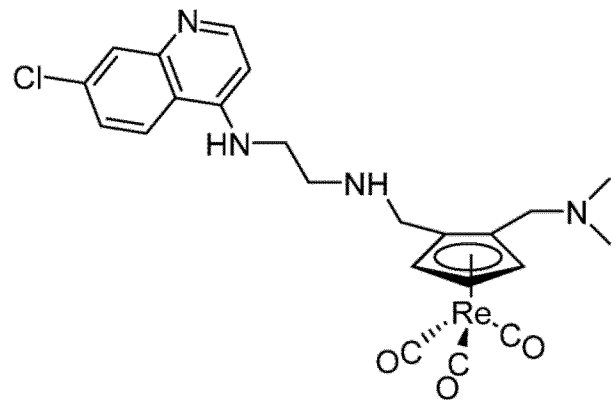

Signed and Sealed this
Twentieth Day of June, 2023

Katherine Kelly Vidal
*Director of the United States Patent and Trademark Office*